United States Patent
Espinoza et al.

(10) Patent No.: US 6,278,034 B1
(45) Date of Patent: Aug. 21, 2001

(54) HYDROGENATION OF HYDROCARBONS

(75) Inventors: Rafael Luis Espinoza, Sasolburg; Andre Peter Steynberg, Vanderbijlpark; Samantha Harding, Parys; Johan Labuschagne, Sasolburg, all of (ZA)

(73) Assignee: Sasol Technology (Proprietary) Limited (ZA)

( * ) Notice: Subject to any disclaimer, the term of this patent is extended or adjusted under 35 U.S.C. 154(b) by 0 days.

(21) Appl. No.: 09/372,638

(22) Filed: Aug. 11, 1999

Related U.S. Application Data (63) Continuation of application No. PCT/GB98/00409, filed on Feb. 10, 1998.

(30) Foreign Application Priority Data

Feb. 20, 1997 (ZA) ........................................... 97-1463
Jan. 23, 1998 (ZA) ........................................... 98-0586

(51) Int. Cl.$^7$ .................................................. C10G 45/16
(52) U.S. Cl. ..................... 585/275; 585/276; 208/144; 208/145; 208/950
(58) Field of Search ................... 208/144, 145, 208/950; 585/275, 276

(56) References Cited

U.S. PATENT DOCUMENTS

| 3,817,856 | | 6/1974 | Aaron et al. ......................... 208/213 |
| 4,102,778 | * | 7/1978 | Ruether ................................ 208/143 |
| 4,111,792 | * | 9/1978 | Caesar et al. ........................... 208/79 |
| 4,624,968 | | 11/1986 | Kim et al. ............................. 518/707 |
| 4,861,746 | | 8/1989 | Oishi et al. ........................... 502/314 |
| 5,308,476 | | 5/1994 | Buttke et al. ......................... 208/157 |
| 5,371,308 | * | 12/1994 | Gosselik et al. ...................... 585/251 |
| 5,527,473 | * | 6/1996 | Ackerman ............................. 210/767 |
| 5,599,849 | * | 2/1997 | Jager et al. ........................... 518/700 |
| 5,766,274 | * | 6/1998 | Wittenbrink et al. .................. 44/436 |
| 5,844,006 | * | 12/1998 | Jager et al. ........................... 518/700 |

FOREIGN PATENT DOCUMENTS

| 0736326 | 10/1996 | (EP) . |
| 9612778 | 5/1996 | (WO) . |

\* cited by examiner

*Primary Examiner*—Bekir L. Yildirim
(74) *Attorney, Agent, or Firm*—Ladas & Parry (57) ABSTRACT

A process for hydrogenating long chain hydrocarbons includes continuously feeding a feedstock having long chain hydrocarbons into a slurry bed including a slurry of catalyst particles in a slurrying liquid. The slurry bed is contained in a reaction zone and the feedstock enters the reaction zone at a low level. A hydrogenation component is fed continuously into the slurry bed, at a low level. The hydrogenation component is allowed to react with the feedstock, to hydrogenate the feedstock, as the feedstock and hydrogenation component pass upwardly through the bed. Hydrogenated long chain hydrocarbons are withdrawn from the reaction zone at a high level, as a hydrogenation product. Any excess hydrogenation component is withdrawn from the reaction zone at a high level.

18 Claims, 7 Drawing Sheets

HYDROGENATION OF HYDROCARBONS

This application is a continuation of PCT/GB98/00409, Feb. 10, 1998.

This invention relates to the hydrogenation of hydrocarbons, in particular long chain hydrocarbon. More particularly, the invention relates to a process for hydrogenating long chain hydrocarbon, and to a catalyst suitable for use in the process.

According to a first aspect of the invention, there is provided a process for hydrogenating long chain hydrocarbon, which process comprises continuously feeding a feedstock comprising long chain hydrocarbon into a slurry bed comprising a slurry of catalyst particles in a slurrying liquid, with the slurry bed being contained in a reaction zone and the feedstock entering the reaction zone at a low level;

continuously feeding a hydrogenation component into the slurry bed, also at a low level;

allowing the hydrogenation component to react with the feedstock, thereby to hydrogenate the feedstock, as the feedstock and hydrogenation component pass upwardly through the slurry bed;

withdrawing hydrogenation long chain hydrocarbon from the reaction zone at a high level, as a hydrogenation product; and withdrawing any excess hydrogenation component from the reaction zone at a high level.

By 'long chain hydrocarbon' is meant hydrocarbons which are in the liquid phase at the operating conditions of the reaction zone.

While the feedstock can, at least in principle, comprise any hydrogen deficient or unsaturated long chain hydrocarbon, the Applicant believes that it may, in particular, comprise a wax fraction. The wax fraction may, more particularly, be that obtained as a product when a syntheses gas is subjected to Fischer-Tropsch reaction conditions. Typically, such a wax fraction may comply with the following: hydrocarbon molecules containing more than 20 carbon atoms; and a congealing point exceeding 90° C.

The feedstock may be in the form of a liquid. In the case where the feedstock is a Fischer-Tropsch derived wax fraction which is normally solid or at least non-fluid at ambient temperature, the feedstock may be at an elevated temperature at which it is fluid. The feedstock may thus be at a temperature between 100° C. and 350° C.

The rate at which the feedstock is fed into the reaction zone will depend on the composition and colour of the feedstock, but may be such as to provide a weight hourly space velocity of at least 0.5, typically about 3.0.

The hydrogenation component is preferably in gaseous form, and may be a hydrogen gas stream or a gas stream rick in hydrogen. The gas stream may be fed into the reaction zone at such a rate that its superficial velocity through the slurry bed is at least 1 cm/s; however, the superficial gas velocity through the slurry bed is preferably at least 5 cm/s.

The gas stream may thus enter the reaction zone through a gas distributor, sparger pipes or the like located at said low level in the reaction zone, with the slurry bed located above and around the gas distributor. The feedstock may then enter the reaction zone in the slurry bed below or immediately above the gas distributor.

The slurrying liquid will, at the bottom of the slurry bed, comprise a mixture of unhydrogenation and hydrogenation long chain hydrocarbons, with the slurrying liquid composition varying as it passes up the slurry bed. Thus, at the point or zone where the hydrogenation product is withdrawn from the slurry bed; the slurrying liquid will comprise mainly hydrogenation long chain hydrocarbons.

The reaction zone may thus be provided by a slurry bed reactor with the gas distributor thus located in or near the bottom of the reactor. A hydrogen feed line will also lead into the bottom of the reactor, eg be connected to the distributor, as will a feedstock flow line. The reactor will then be operated so that a slurry bed/gas interface is located some distance from the top of the reactor, ie so that a gas head or vapour space is provided above the slurry bed. An excess hydrogen gas withdrawal line will then lead form a gas outlet at the top of the reactor so that it is in communication with the head space. A hydrogenation product withdrawal line will lead from the reactor at a level below the level of the interface.

The gas velocity in the vapour space between the slurry bed/gas interface and the gas outlet should be low enough to avoid significant entrainment of slurry or slurry components in the outlet gas. Typically, this can be equal to the superficial gas velocity at the top of the slurry bed, to avoid complicating the reactor design by having to adjust the reactor diameter above the top of the bed. A typical gas velocity in the vapour space is therefore of at least 5 cm/s.

The concentration of the catalyst particles in the slurry bed may be between 10 mass % and 50 mass %, based on the total slurry bed mass. The slurry bed may be maintained at a temperature between 180° C. and 300° C., while the reaction zone may be maintained at a pressure between 10 atmospheres and 50 atmospheres.

Separation of the hydrogenation product from the catalyst particles of the slurry bed can be effected either internally in the reactor or externally thereof, using any suitable particle separation system such as a decanter, hydrocyclone or filter.

Excess hydrogen withdrawn from the top of the reactor can naturally be recycled to the gas distributor. The excess hydrogen may then typically be cooled to below 70° C., recompressed, and reheated to above 100° C., prior to being reintroduced into the reactor.

The reactor walls may be heated by means of a steam jacket in order to control the reactor temperature. For large reactors, it is expected that steam pipes, located inside the reactor, may be used.

The catalyst particles may have a size distribution between 1 and 250 microns, preferably between 30 and 170 microns. The catalyst should preferably not degrade to smaller particle sizes to any significant extent over extended periods of time. For example, less than 10% of particles below 30 microns should preferably be produced during a three month period of operation of the reactor; some variations hereof may be acceptable depending on reactor design, product value, feedstock cost and the cost of catalyst replacement.

Preferably, the catalyst may be that obtained by (i) subjecting a slurry, comprising a particulate alumina or silica carrier, a nickel compound as an active component and a solvent for the active component, to a sub-atmospheric pressure environment, thereby to impregnate the carrier with the active component;

(ii) drying the impregnated carrier in a sub-atmospheric pressure environment; and (iii) calcining the dried impregnated carrier, thereby to obtain a hydrogenation catalyst suitable for use in the hydrogenation process.

Thus, according to a second aspect of the invention, there is provided a process for the preparation of a hydrogenation catalyst suitable for use in a hydrogenation reaction of long chain hydrocarbons, the process comprising (i) subjecting a slurry, comprising a particulate alumina or silica carrier, a nickel compound as an active component and a solvent for the active component, to a sub-atmospheric pressure environment, thereby to impregnate the carrier with the active component;

(ii) drying the impregnated carrier in a sub-atmospheric pressure environment; and (iii) calcining the dried impregnated carrier, thereby to obtain a hydrogenation catalyst suitable for use in a hydrogenation reaction of long chain hydrocarbons.

Still further, according to a third aspect of the invention, there is provided a process for the preparation of a hydrogenation catalyst suitable for use in a hydrogenation reaction of long chain hydrocarbons, the process comprising (i) preparing a particulate alumina or silica carrier;

(ii) forming a slurry of the particulate alumina or silica carrier, a nickel compound as an active component and a solvent for the active component;

(iii) subjecting the slurry to a sub-atmospheric pressure environment, thereby to impregnate the carrier with the active component;

(iv) drying the impregnated carrier in a sub-atmospheric pressure environment; and (v) calcining the dried impregnated carrier, thereby to obtain a hydrogenation catalyst suitable for use in a hydrogenation reaction of long chain hydrocarbons.

The nickel compound may be in the form of nickel nitrate. This compound is water soluble, and the solvent may thus be water.

The sub-atmospheric pressure environment during the impregnation may be at a pressure less than 20 kPa (a), and preferably at a pressure less than 10 kPa (a). Likewise, the sub-atmospheric pressure environment during the drying may be at a pressure less than 20 kPa (a), and preferably at a pressure less than 10 kPa (a). Should the impregnation and drying steps take place at higher pressures, eg at atmospheric pressure, it will have a detrimental effect on the dispersion of the nickel compound and therefore in the metal surface area of the catalyst and on its catalytic activity.

The sub-atmospheric pressure environment can thus be obtained by locating the slurry in a suitable enclosed vessel, and drawing the required sub-atmospheric pressure or vacuum on the vessel.

While the impregnation and drying under sub-atmospheric pressure or vacuum environments or conditions can be effected in tow separate or distinct steps, they can, if desired, be effected in a single step, so that the impregnation is effected while the drying takes place.

The drying in said sub-atmospheric pressure environment may be continued until the moisture content of the impregnated carrier is below a predetermined level, eg below 20% by mass. Thereafter, the impregnated carrier may be dried further prior to the calcining and/or the calcining may be effected, under non-sub-atmospheric pressure conditions. The further drying or calcining may be effected by passing a drying medium, eg air, in counter-current fashion over the impregnated carrier.

If desired, the dried impregnated carrier and/or the calcined catalyst can be re-slurried with water and fresh active component, for further impregnation as hereinbefore described. This impregnation may also be effected in a sub-atmospheric pressure environment. The resultant further impregnated carrier can the again be subjected to the drying and calcination as hereinbefore described.

The slurry may be formed by initially dissolving the active component in at least some of the solvent prior to forming the slurry with the carrier, so that formation of the slurry will then involve intimate admixing of the carrier and a solution of the active component.

The resultant catalyst may be washed with a suitable washing medium, eg water, after the calcination, to remove unwanted contaminants, such as nickel, which may have formed on the external surface of the catalyst in the form of a shell of nickel, ie without carrier being present in the shell. This washing is preferably effected with agitation, which may be achieved through boiling of the water in which the catalyst is washed. The water may be changed from time to time to speed up the procedure. Failure to perform this washing step may result in the appearance of small particles of the containment in the hydrogenation products.

The calcined catalyst may, prior to use, be reduced, eg by subjecting it to heat treatment under the influence of a reducing gas such as hydrogen.

The carrier may be pretreated prior to forming the slurry thereof with the solvent and the active component. This pre-treatment may comprise precalcining the carrier prior to slurry formation. This calcination may be effected at a temperature between 200° C. and 1150° C., preferably between 400° C. and 1100° C.

The carrier or support may be that prepared by a spray-drying technique, provided that it has been subjected to the calcination temperature hereinbefore referred to, either during manufacture thereof, or subsequently during pretreatment thereof a hereinbefore described.

The carrier may, during preparation thereof, be manipulated to modify its pore size distribution to maximize or at least enhance the dispersion of the active component on the carrier surface while at the same time maximizing or at least enhancing the diffusion of the large hydrocarbon molecules into and out of the pores of the resultant hydrogenation catalyst, during use in hydrogenating long chain hydrocarbons.

The manipulation may comprise using pore regulating agents such as polyacrylamide (PAA) or polyvinyl alcohol (PVA) during the synthesis of the silica or alumina.

The manipulation may instead, or in addition, comprise mixing other substances such as carbon black or wax particles or other pore modifying agents with the alumina or silica. This mixing can take place with the alumina or silica either being in a gel phase or being in the form of non-porous nano-particles, prior to the spray drying of such gel or nano-particles to produce the carrier.

The manipulation may instead or in addition comprise calcination of the carrier and/or steaming thereof, in the presence or absence of other chemicals such as ammonia, or calcination followed by steaming followed by calcination.

The mass % of the active component in the carrier may be between 10% to 45%, typically between 15% to 40%, based on the total combined mass of the carrier and the active component.

The invention extends also to a hydrogenation catalyst when prepared by the process as hereinbefore described, and to a hydrogenation product when produced by a process as hereinbefore described.

The invention will now be described in more detail with reference to the accompanying drawings and non-limiting examples.

Figure 1:
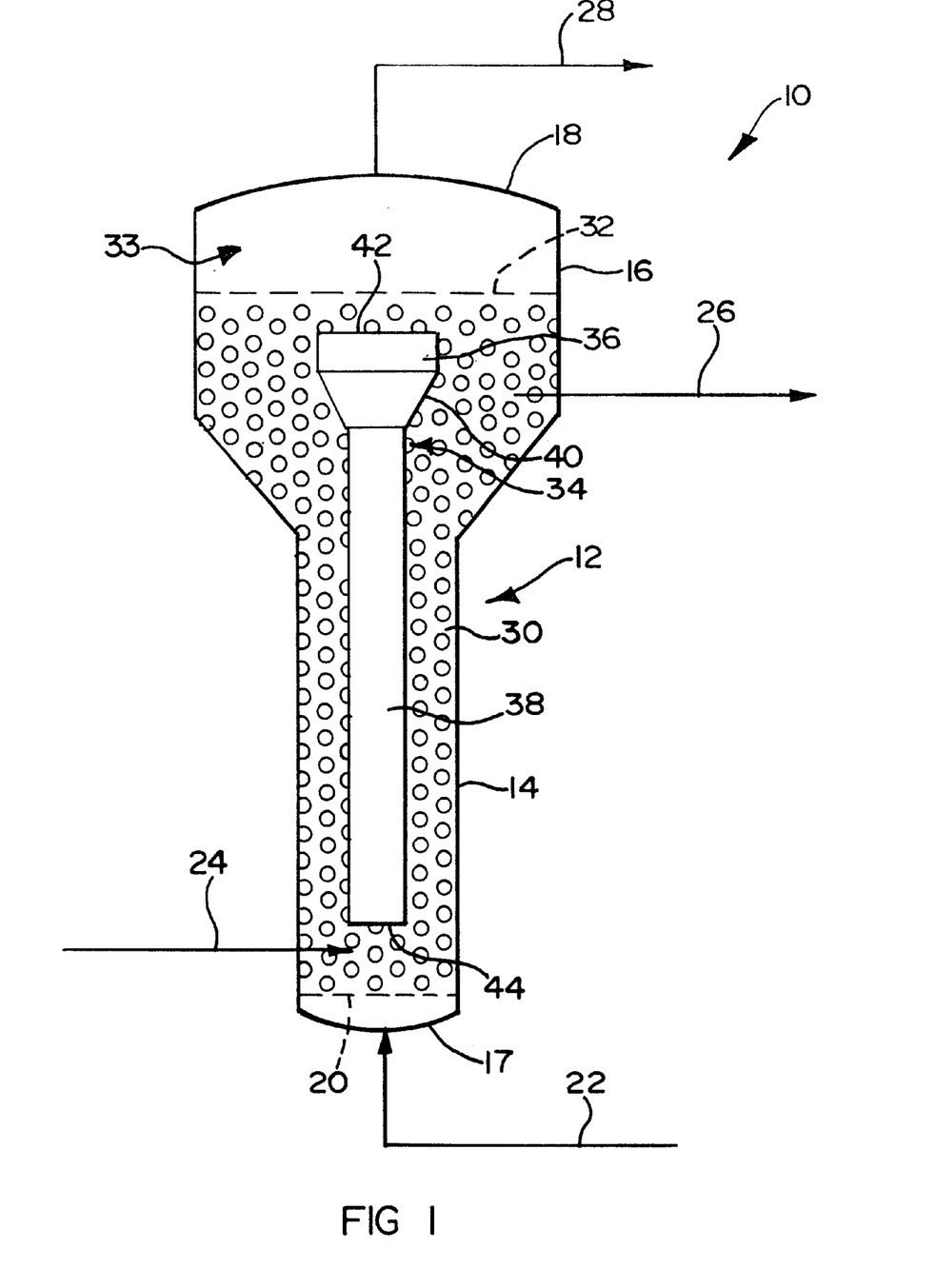
FIG. 1 show, diagrammatically, a process according to the invention for hydrogenating long chain hydrocarbons, with the process including a slurry bed reactor.

Referring to FIG. 1, reference numeral 10 generally indicates a process according to the invention for hydrogenating long chain hydrocarbons. The process 10 includes a reactor 12.

The reactor 12 comprises a lower narrow reactor portion 14 of relatively small diameter, flaring into a upper portion 16 of larger diameter. The lower end of the narrow reactor portion 14 is closed off with an end piece 17 while the upper end of the portion 16 is closed off with a roof 18. An apertured gas distributor 20 is located inside the narrow reactor portion 14 at its lower end, with a hydrogen feed line 22 leading into the lower end of the narrow reactor portion 14, below the gas distributor 20.

A long chain hydrocarbon feedstock feed line 24 leads into the lower end of the narrow reactor portion 14, immediately above the gas distributor 20. A hydrogenated liquid product withdrawal line 26 leads from the upper portion 16 of the reactor 12, while an unreacted hydrogen withdrawal line 28 leads from the roof 18.

A mixing device in the form of a downcomer 34 is located inside the reactor 12. The downcomer 34 acts to keep the catalyst concentration profile and the temperature profile along the length of the reactor 12 as even a possible. The downcomer 34 comprises a degassing section 36 having a relatively large diameter and located within the upper portion 16 of the reactor 12. The downcomer 34 also comprises a transport section 38 of smaller diameter, and located within the reactor portion 14. The degassing section 36 and the transport section 38 are connected together by means of a faltered section 40. The downcomer 34 thus has an open upper end 42 as well as an open lower end 44 of smaller diameter than the upper end 42. The downcomer is thus located within a slurry bed 30 of catalyst particles suspended in long chain hydrocarbons, with the upper end 43 being located below a slurry bed/gas interphase 32.

In other embodiments (not shown), the transport section 38 and part of the degassing section 36 can be located outside the reactor 12, with the outlet end 44 of the transport section then being located inside the reactor 12.

In use, a Fischer-Tropsch derived wax fraction having a typical boiling range temperature of up to 500° C., is preheated (not shown) to a temperature of at least 100° C. to ensure that it is in liquid form, before being fed continuously into the lower end of the narrow reactor portion 14 to form part of the slurry bed 30. At the lower end of the narrow reactor portion 14, the catalyst particles will be suspended, in the slurry bed 30, in a mixture of hydrogenation and non-hydrogenation long chain hydrocarbons, while towards the upper end of the bed 30, ie in proximity to a slurry bed/gas interface 32, the catalyst particles will be suspended in substantially hydrogenation long chain hydrocarbons. The feedstock is introduced into the reactor 12 at such a rate that the liquid hourly space velocity therein is about 3.0.

Hydrogen is continuously introduced into the bottom of the narrow reactor portion 14, along the flow line 22. Sufficient hydrogen is introduced so that the superficial gas velocity through the slurry bed 30 is about 5 cm/s.

Sufficient catalyst is used such that its concentration in the slurry bed is between about 10 mall % and about 50 mass %, typically about 35 mass %. The slurry bed is typically maintained at a temperature of about 240° C.

The catalyst particles are typically in the range 30 to 170 microns, and a catalyst as hereinafter described with reference to Examples 1 to 15, can be used.

Unreacted hydrogen separates from the slurry bed 30 at the slurry bed/gas interface 32 enters a head space 33 above the slurry bed 30, and is withdrawn continuously along the flow line 28. This hydrogen can be recycled (not shown).

Hydrogenated long chain hydrocarbon product is withdrawn continuously form the reactor 12 along the flow line 26. The liquid product is separated form the catalyst particles either by means of internal separation (not shown) or by way of external separation (not shown).

The degassing section 36 of the downcomer 34 permits the bulk of the gas bubbles to escape from fluidized slurry that enters the upper end 42 of the downcomer 34. For this purpose, the diameter of the degassing section 36 is sized such that the downward slurry flow in the degassing section 36 is lower than that of the rise velocity of a selected bubble size. The cross-sectional area of the degassing section 36 is between 2% and 50%, preferably between 6% and 25%, of the cross-sectional area of the reactor at the same level. The vertical height of the degassing section 36 is sized to allow sufficient time for the gas bubbles of a selected size to rise out of the degassing section. This height is typically between 0.229 m and 0.609 m, preferably between 0.305 m and 0.508 m. The shape of the degassing section 36 is determined by the shape and configuration of the reactor 12 as well as by the space available inside the reactor. In typical applications the degassing section 36 is cylindrical but it can instead, for example, be in the form of a rectangular or triangular channel (not shown).

The transport section 38 of the downcomer serves to transport the degasssed slurry to a lower point in the reactor 12. The flow of slurry through the downcomer results from the density difference between the partially or completely degassed slurry in the transport section of the downcomer, and the aerated slurry on the outside of the downcomer. Provided that efficient degassing takes place in the degassing section 36, the length and internal diameter of the transport section are the main components of the downcomer which determine the slurry flow rate achievable in the downcomer at a particular set of operating conditions. This is due to the fact that the length and internal diameter of the transport section determine the friction loss in the downcomer. The slurry flow rate achieved in the downcomer is a balance between the density driving force, provided by the density difference hereinbefore referred to, and the friction loss in the downcomer.

The slurry flow rate inside the downcomer can be between 0.5 and 10 m/s, but is preferably between 2 m/s and 5 m/s. Thus, the slurry flow rate in the downcomer should preferably be below about 5 m/s to prevent both erosion of the downcomer and physical degradation of the catalyst in the slurry. The minimum flow rate in the downcomer is such that the upward superficial liquid velocity in the reaction zone of the reactor is sufficient to prevent significant catalyst settling. The upward superficial liquid velocity on the outside of the downcomer can be between 0.5 cm/s and 10 cm/s, but preferably is between 2 cm/s and 4 cm/s.

In typical applications, the total length of the transport section of the downcomer can be between 0.3 m and 32 m, but preferably is between 4 m and 15 m.

The position of the bottom outlet end 44 of the downcomer is such that impingement of degassed slurry onto the reactor wall or reactor internals is minimized. Such impingement may lead to erosion or physical degradation of the catalyst over a period of time. The position of the downcomer outlet end 44 relative to the gas distributor 20 must be such that even distribution of gas into the slurry bed 30 is not adversely effected.

Settling of catalyst in the downcomer 34 must be prevented. Thus, the angle of the walls of the section 40 of the downcomer should not exceed the angle of repose of the slurry.

Figure 2:
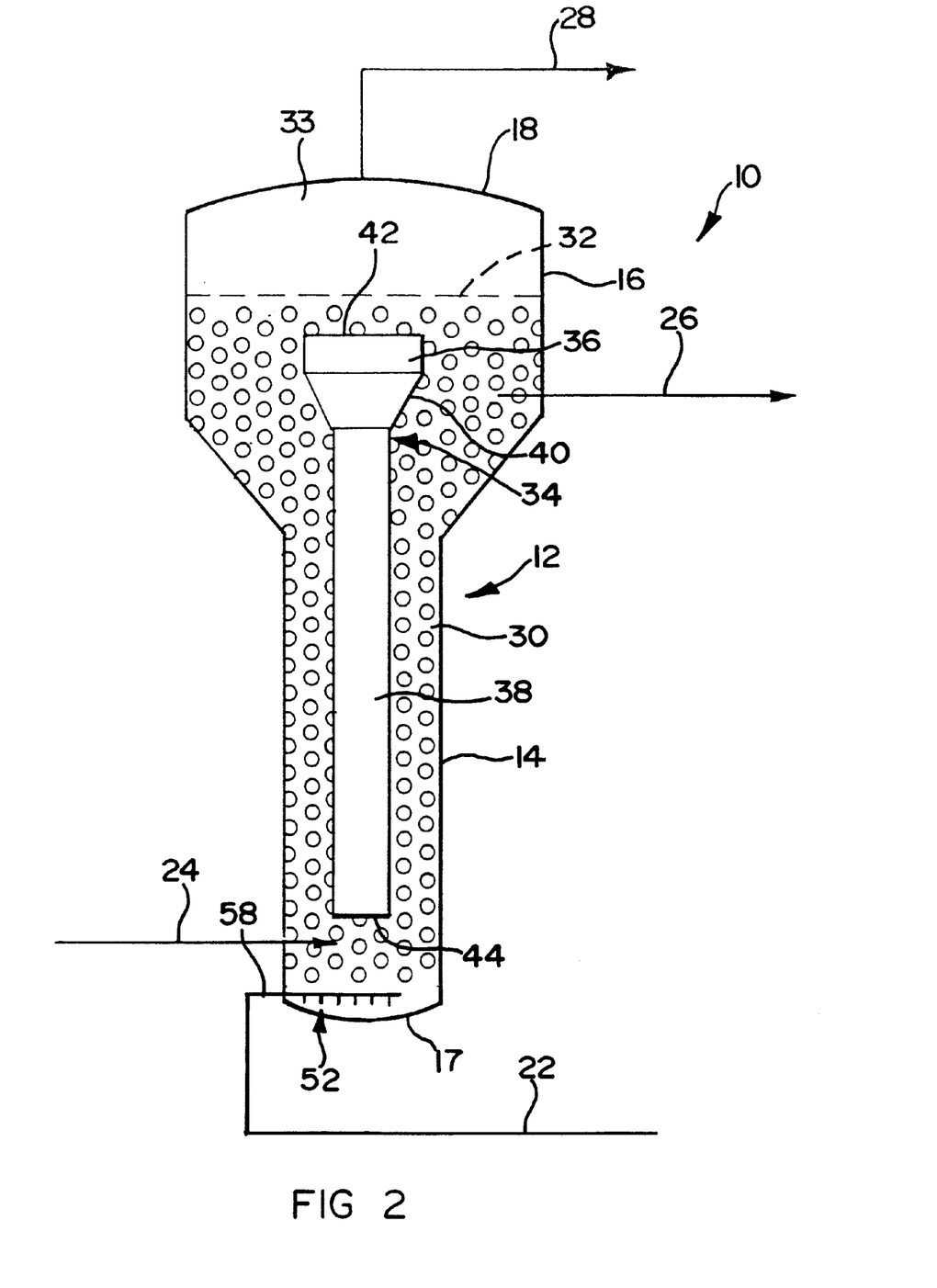
FIG. 2 shows, diagrammatically, a different slurry bed reactor which can be sued in the process of FIG. 1.
Figure 3:
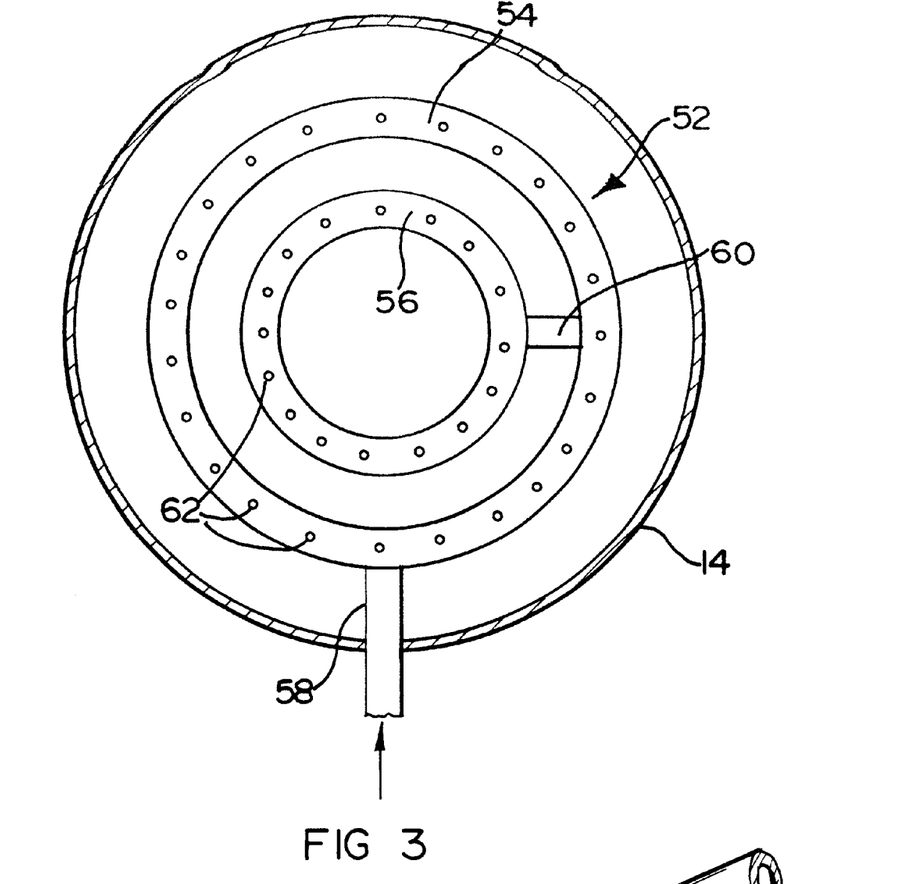
FIG. 3 shows an enlarged view from the bottom of the sparger of the reactor of FIG. 2.
Figure 4:
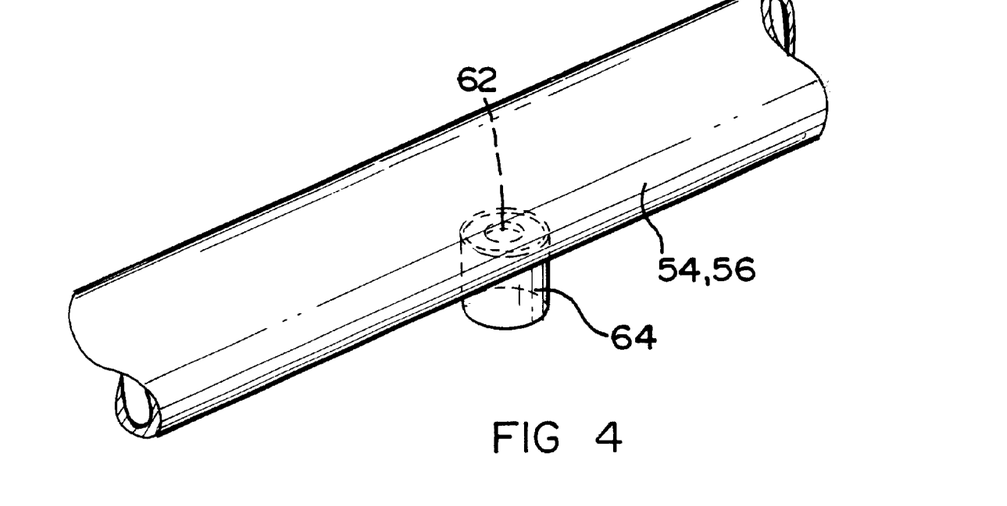
FIG. 4 shows an enlarged three-dimensional view of a portion of the sparger of FIG. 3.

Referring to FIGS. 2 to 4, reference number 50 generally indicate a different slurry bed reactor which can be used in the process 10 of FIG. 1.

Parts of the reactor 50 which are the same or similar to those of the reactor 12, are indicated with the same reference numerals.

Instead of having a gas distributor 20, the reactor 50 includes a gas sparger 52. The sparger 52 typically comprises two concentric ring-like sparger pipes 54, 56, with the pipe 56 being located inside the pipe 54. A gas inlet pipe 58 leads into the outer sparger pipe 54, with the hydrogen feed line 22 connected to the inlet pipe 58. A connecting pipe 60 connects the sparger pipes 54, 56.

Each of the sparger pipes 54, 56 is provided with a plurality of downwardly directed gas apertures 62. The gas apertures 62 are thus spaced apart circumferentially along the sparger pipes 54, 56. Around each aperture 62 is provided a length of pipe 64. The apertures 62 serve to provide pressure drop of gas from the sparger pipe 54, 56 into the reactor, while the pipes 64 reduce the velocity of the gas before it enters the slurry bed 30. However, the pipes 64 can be omitted, if desired.

The apertures 62 are sized to produce a pressure drop of between 5% and 90% of the reactor pressure drop, preferably between 20% and 40% of the reactor pressure drop.

Instead of the apertures 62 being downwardly directed they can, if desired, be upwardly directed. The apertures 62 need also not necessarily be spaced evenly apart circumferentially along the sparger pipes 54, 56 but any desired arrangement thereof can be sued. Additionally, the sparger 52 need not necessarily comprise two concentric sparger pipes 54, 56 but any desired sparger pipe configuration can be used.

The sparger 52 is located close to the end piece 17 of the reactor 50.

In laboratory scale simulations of the process 10, a series of catalysts comprising nickel supported on silica or alumina carriers, were prepared and tested for their performance in the hydrogenation of a wax fraction obtained from a Fischer-Tropsch process. The effectiveness of the catalyst as a wax hydrogenation catalyst is measured by the Saybolt colour of the hydrogenation wax. Thus, the higher the Saybolt colour of the hydrogenation wax, the more effective is the catalyst as a wax hydrogenation catalyst. In each case a similar wax fraction was used.

TESTING PROCEDURE

IN each test, reduction of the catalyst to be tested was carried out at atmospheric pressure using pure hydrogen (purity of 99.999%) in a fluidised bed at a flow rate of 0.5 liters (normal) per minute. Twenty grams of catalyst was loaded in a glass tube and heated up to the desired reduction temperature over a period of 6 hours. The catalyst was kept at the desired reduction temperature for a period of 16 hours, after which it was allowed to cool down to 100° C., whereafter the hydrogen was replaced with argon. The catalyst was then transferred into 30 g molten unhydrogenation Fischer-Tropsch wax under an argon atmosphere and allowed to cool down to room temperature. At room temperature, the catalyst containing Fischer-Tropsch wax was congealed.

500 g of the same unhydrogenation Fischer-Tropsch derived was loaded into a slurry bed reactor (which thus simulated the reactor 12) equipped with a mechanical stirrer and heated under a nitrogen blanket. The boiling temperature of this was ranged between 370° C. and 500° C. The solid mixture of the externally reduce wax hydrogenation catalyst (20 g) and unhydrogenation wax (30 g) was added to the reactor, and the slurry bed reactor closed. The reactor was flushed with nitrogen from a cylinder (purity of 99.995%), the pressure increased to 30 bar and the temperature increased to 180° C. The stirrer speed was 320 rpm. Hydrogen was then introduced at a flow rate of 0.8 liters (normal) per minute, and the wax was hydrogenation at 180° C. for 4 hours. The hydrogenation was terminated by replacing the hydrogen with nitrogen whilst rapidly decreasing the pressure to atmospheric and cooling the system. At approximately 150° C., the reactor was unloaded and the wax filtered through Watman no. 42 filter paper at 130° C. under an argon blanket.

The colour of the hydrogenation, filtered wax was measured on a Colorgard System/05 (trademark) apparatus manufactured by Pacific Scientific, and the result translated to the corresponding Saybolt number.

Examples 1 to 12, 14 and 15 deal with the preparation of hydrogenation catalysts suitable for use in the hydrogenation process of the invention.

EXAMPLE 1

44.6 g of $Ni(NO_3)_2.6H_2O$ as an active component were dissolved in 50 ml distilled water. 50 g of $Al_2O_3$ carrier (Puralox SCCa 5/150) (trade mark) obtainable from Condea Chemie GmbH of Uberseering 40, 22297 Hamburg, Germany, were added to this solution, to form a slurry. This slurry was vacuum dried for ~3.5 hours in a rotary evaporator with an oil bath temperature of 75° C. and a pressure of 71 mbar(a), so that impregnation of the nickel compound into the carrier is effected simultaneously with the drying. This sample was thereafter further dried in a fluidised bed at 150° C. for 1 hour followed by calcining at 300° C. for 4 hours. The calcined sample was re-slurred in a solution of 29.7 g $Ni(NO_3)_2.6H_2O$ dissolved in 50 ml distilled water. The slurry was again impregnated and dried in a rotary evaporator with an oil bath temperature of 75° C. and a pressure of 71 mbar(a) for ~3.5 hours. It was further dried in a fluidised bed for 1 hour at 150° C. and then calcined in air for 4 hours at 300° C.

EXAMPLE 2

The preparation of the catalyst of this Example was similar to that of Example 1 except that Puralox SCCa 5/90 (trademark), also obtainable from Condea Chemie GmbH, was used as the carrier or support instead of Puralox SCCa 5/150 (trademark).

EXAMPLE 3

43.8 g of $Ni(NO_3)_2.6H_2O$ were dissolved with 43.8 g or urea in 250 ml distilled water. 50 g of $Al_2O_3$ carrier (Puralox SCCa 5/150) (trademark) were added to the solution. The slurry was then put on the rotary evaporator in a closed system for 12 hours with an oil bath temperature of 80° C. A further solution of 43.8 g of Ni(NO$_3$)$_2$.6H$_2$O, 43.8 g urea and 250 ml distilled water was added to the slurry and the reaction was continued for another 12 hours. A final solution of 43.8 g Ni(NO$_3$)$_2$.6H$_2$O, 43.8 g urea and 250 ml distilled water was added and the slurry was put on the rotary evaporator under the same conditions for a further 12 hours. The slurry was then washed out with distilled water until no more nickel nitrate washed out. The washed slurry was dried on the rotary evaporator at 75 mbar (a) with an oil bath temperature of 75° C. It was further dried in a fluidised bed for 1 hour at 150° C. and then calcined for 4 hours at 300° C. in air.

EXAMPLE 4

The preparation of this catalyst was similar to that of Example 3 with the following differences:
1. Purlaox SCCa 5/90 (trademark) replaced Puralox SCCa 5/150 as the support; and
2. Only one post-addition of Ni(NO$_3$)$_2$.6H$_2$O was made to the slurry and the slurry was washed with distilled water before the addition.

EXAMPLE 5

The preparation of this catalyst was similar to that of Example 3 except that 38.8 g Ni(NO$_3$)$_2$.6H$_2$O and 34.5 g urea in 50 ml distilled water were added to the 50 g SCCa 5/150 (trademark) as carrier. The slurry was held under the same conditions as Example 3 for 16 hours. No post additions of Ni(NO$_3$)$_2$.6H$_2$O were made before washing.

EXAMPLE 6

74.3 g of Ni(NO$_3$)$_2$.6H$_2$O were dissolved in 50 ml of distilled water. 1.5 ml HNO$_3$ (55% by vol) were added to the solution. This was then added to 50 g of Aluminium Oxide C (trademark) carrier obtainable from Degussa AG, Gesh äftsbererch Anorganische Chemieprodukte, Postfach 110533, D-6000 Frankfurt 11, Federation Republic of Germany. The paste was kneaded for 2 hours at atmospheric pressure and the sample was then over dried at 120° C. overnight. The dried sample was crushed and sieved to between 38 and 150 microns after which it was oven dried for a further 1 hour at 150° C. in a fluidised bed followed by calcination for 4 hours at 300° C. in air.

EXAMPLE 7

The preparation of this catalyst was similar to that of Example 2, except that the pH of the impregnating solution was adjusted to 2 with nitric acid.

EXAMPLE 8

The preparation of the catalyst was similar to that of Example 2, except that the catalyst was calcined in an oven (not fluidised) for 1 hour at 350° C.

EXAMPLE 9

Sipernat 22 (trademark), available from Degussa AG, is a large pore size, large pore volume SiO$_2$. 74.36 g of Ni(NO$_3$)$_2$.6H$_2$O was dissolved in 150 ml H$_2$O. 50 g of Sipernat 22 was added to the solution and the slurry dried, calcined and reduced according to the procedure described for Example b 1.

EXAMPLE 10

C500-109 (trademark) is a high surface area, large pore volume SiO$_2$ support available from Engelhard de Meern B. V., Strijkviertel 67, PO Box 19, Ni-3454 ZG DeMeern, The Netherlands. The catalyst preparation on C500-109 in this Example was similar to that described in Example 1 except that the amount of H$_2$O added to form the slurry was greater (175 ml in the first and 120 ml in the second impregnation steps) due to the high pore volume of the carrier.

EXAMPLE 11

The catalyst preparation in this Example and which was also based on C500-109 (trademark) (50 Ni/100 SiO$_2$), was similar to that described in Example 1, except that the first impregnation solution was 74.30 g Ni(NO$_3$)$_2$.6H$_2$O in 150 ml H$_2$O, while the second impregnation solution was 49.54 g Ni(NO$_3$)$_2$.6H$_2$O in 100 ml H$_2$O.

EXAMPLE 12

This catalyst was prepared in the same manner as that described in Example 6, up to the point of drying. In Example 6, the catalyst was dried in an oven and then crushed. In this case, it was diluted with water to a sprayable viscosity and then spray dried in a Niro (trademark) atomsier. Spray dried particles are more spherical and would be more abrasion resistant. The spray dried catalyst was calcined and reduced in a similar manner to that described in Example 1. The reduction temperature was 380° C.

Results

Characterization of the catalysts of Examples 1 to 12, and their performance for Fischer-Tropsch was hydrogenation, are shown in Table 1. Fischer-Tropsch wax comprises a mixture of long chain saturated and unsaturated hydrocarbons.

In Table 1, 'TPR' means Temperature Programmed Reduction. Also 'Nickel loading' means mass % of Ni added to catalyst, while 'metal dispersion' means the degree to which the Ni is dispersed or distributed in or on the catalytic carrier/support.

TABLE 1

| | CHARCTERIZATION OF THE NICKEL CATALYST | | | | | | | | |
|---|---|---|---|---|---|---|---|---|---|
| EXAMPLE | Nickel Loading (%) | Area (m$^2$/g) | Pore Volume (ml/g) | Pore Size (A) | Metal Dispersion (%) | TPR Peak · max (° C.) | Hydrogenated Wax Colour (Saybol) | Red. Temp (° C.) | Metal (Ni) Surface Area (m$^2$/g Catalyst) |
| 1 | 20.3 | 140 | 0,23 | 65,1 | 15,7 | 273;402 | 5 | 380 | 22,3 |
| 2 | 18,4 | 89 | 0,22 | 98,9 | 9,7 | 288;490 | 17 | 380 | 12,8 |
| 3 | 12,7 | 165 | 0,35 | 84,9 | 12,4 | 257;461;531 | 5 | 285 | 11,0 |

TABLE 1-continued

CHARCTERIZATION OF THE NICKEL CATALYST

| EXAMPLE | Nickel Loading (%) | Area (m²/g) | Pore Volume (ml/g) | Pore Size (A) | Metal Dispersion (%) | TPR Peak · max (° C.) | Hydrogenated Wax Colour (Saybol) | Red. Temp (° C.) | Metal (Ni) Surface Area (m²/g Catalyst) |
|---|---|---|---|---|---|---|---|---|---|
| 4  | 16,0 | 117 | 0,26 | 88,9  | 10,2 | 236;312;426 | 14 | 380 | 11,4 |
| 5  | 9,9  | 156 | 0,38 | 97,2  | 16,4 | 306;401;530 | 7  | 380 | 11,3 |
| 6  | 23,0 | 90  | 0,39 | 175,1 | 4,9  | 270;378;514 | 22 | 380 | 8,0  |
| 7  | 21,0 | 76  | 0,23 | 121,1 | 8,5  | 228;406;530 | 16 | 380 | 12,5 |
| 8  | 20,2 | 86  | 0,22 | 102,5 | 11,6 | 222;398;500 | 19 | 425 | 16,4 |
| 9  | 22,0 | 123 | 0,75 | 243,7 | 0,5  | 221;400     | 2  | 380 | 0,5  |
| 10 | 21,8 | 218 | 0,88 | 162,5 | 3,4  | 207;365     | 16 | 380 | 5,2  |
| 11 | 29,6 | 172 | 0,77 | 179,0 | 2,8  | 357         | 17 | 425 | 6,8  |
| 12 | 18,8 | 76  | 0,47 | 245,8 | 5,7  | 229;416;507 | 15 | 380 | 7,4  |

Figure 5:
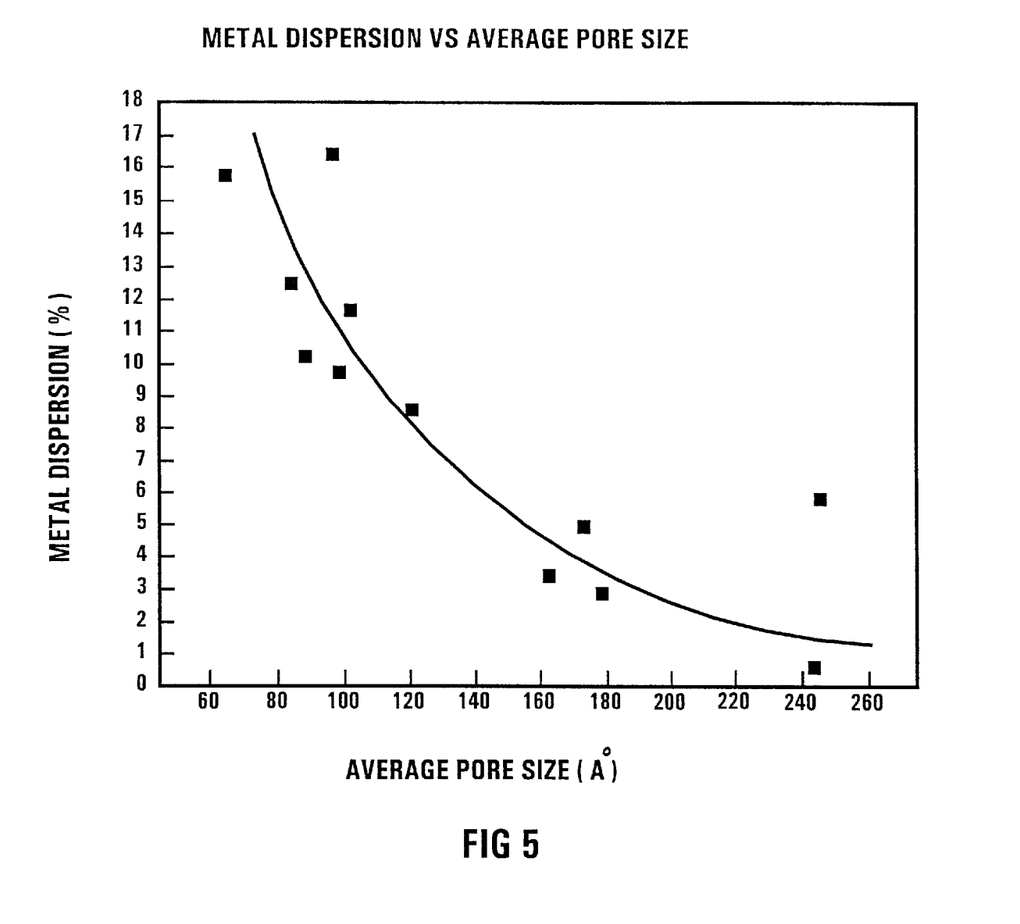
FIG. 5 shows, in respect of some of the hydrogenation catalysts of Examples 1 to 12, the metal dispersion of the active component vs the average pore size of the catalyst.

The following conclusions are evident from Table 1:

The dispersion of the active component (nickel) is, strongly, a function of the average pore size of the catalyst, although the nature of the carrier, the total amount of the active component and the specific catalyst preparation method also play a role. This is illustrated in FIG. 5, which shows the dispersion of the active component vs the average pore size of some of the catalysts of Examples 1 to 12.

The intrinsic activity of metal supported catalysts is a function of the metal area of the active component. This metal area depends on the total amount of active component and on its dispersion. Thus, the metal area of the active component increases with the dispersion of the active component and with the total amount of active component in the catalyst.

Figure 6:
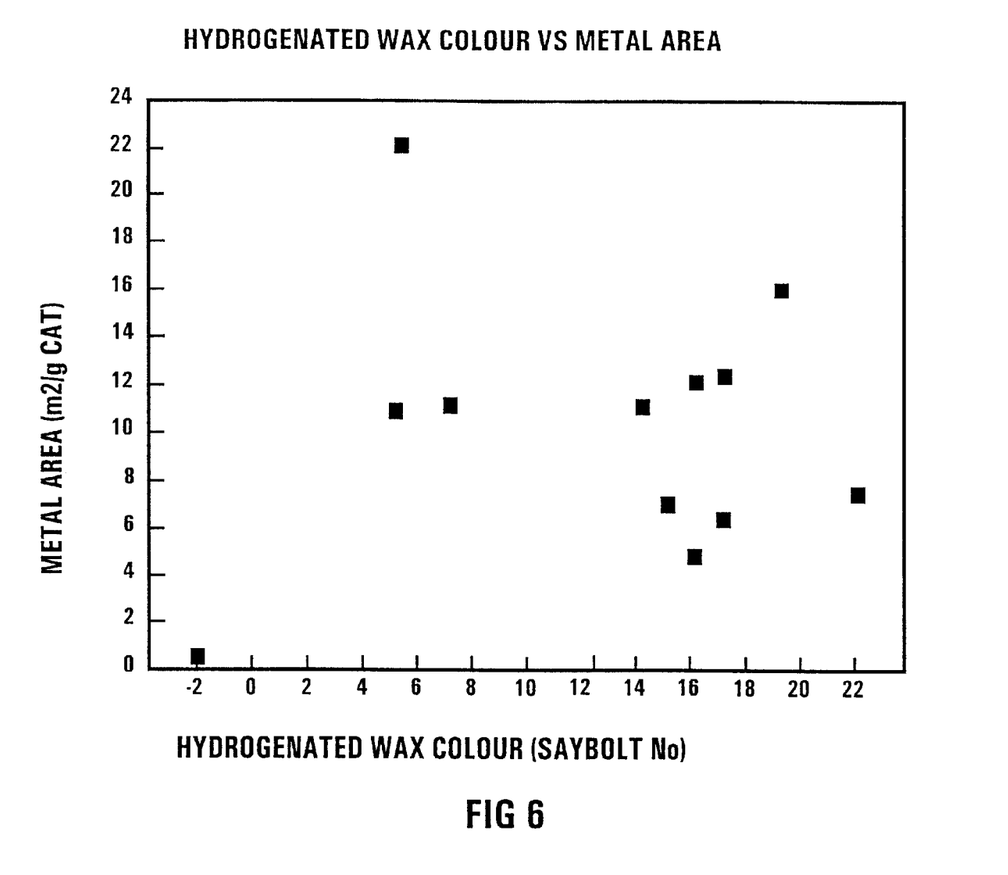
FIG. 6 shows, in respect of some of the hydrogenation catalysts of Examples 1 to 12, the catalyst performance vs the total metal area of the active compound in the catalyst.

Thus, normally, the higher the metal area of the active component in a catalyst, the better its performance for the hydrogenation of a Fischer-Tropsch wax. In other words, normally, the higher the metal area of the active component, the higher the Saybolt colour of the Fischer-Tropsch wax as a result of its hydrogenation. The results shown in Table 1, however, do not support this expected behaviour, and are depicted in FIG. 6, in which the Saybolt colour of the hydrogenated wax vs the metal area of the active component is plotted.

Fischer-Tropsch waxes can be hydrogenated comprise a mixture of paraffinic, olefinic and oxygenated long chain hydrocarbons. Typically, the length of these hydrocarbons is from about $C_{20}$ up to $C_{80}$ and higher. Because of this, diffusion of the wax hydrocarbon molecules into and out of the catalyst pores is expected to play an important role in the overall catalyst performance. It is well known by those skilled in the art that the diffusion of these large molecules increases with increasing catalyst pore size.

Figure 7:
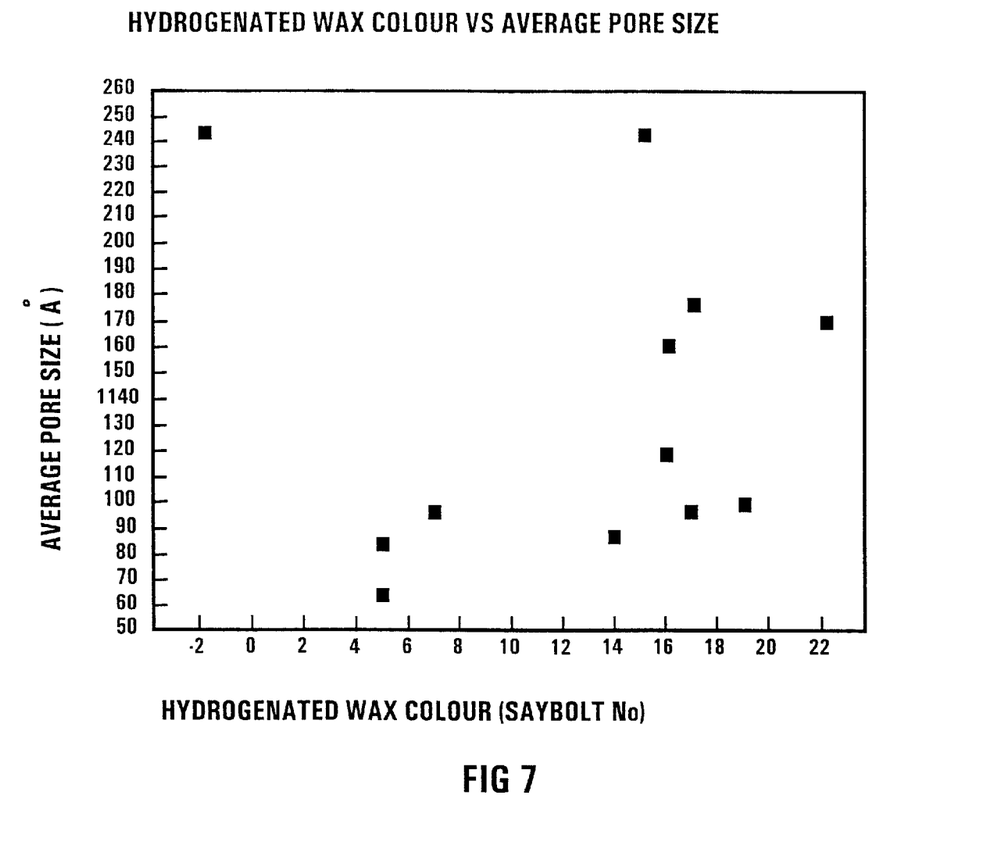
FIG. 7 shows, in respect of some of the hydrogenation catalysts of Examples 1 to 12, catalyst performance vs average pore size of the catalyst.

To ascertain whether the catalyst performance is solely linked to the catalyst pore size, the Saybolt colour of the hydrogenated Fischer-Tropsch wax vs the average pore size of the catalyst was plotted (FIG. 7). From FIG. 7, it can be seen that there is some correlation between the catalyst performance and its average pore size. Higher pore sizes seem to be linked to a higher wax colour, as expressed in Saybolt units.

It seems, therefore that more than one parameter is responsible for the performance of the hydrogenation catalyst.

To ascertain the importance of both the diffusion and the metal area of the active component in the overall performance of our hydrogenation catalyst, the following correlation, which includes the total metal area of the active component as well as the average catalyst pore size, was developed:

$$\text{Overall Catalyst Performance Factor (OCPF)} = \text{Total metal area of the active component} \times \left[\text{Average pore size of the catalyst}\right]^2 \quad \text{Eq (1)}$$

where,
The overall catalyst performance is measured as Saybolt colour of the hydrogenated wax
The total metal area of the active compound is expressed as m² per gram of catalyst.
The average pore size of the catalyst is expressed in Amstrongs.

Figure 8:
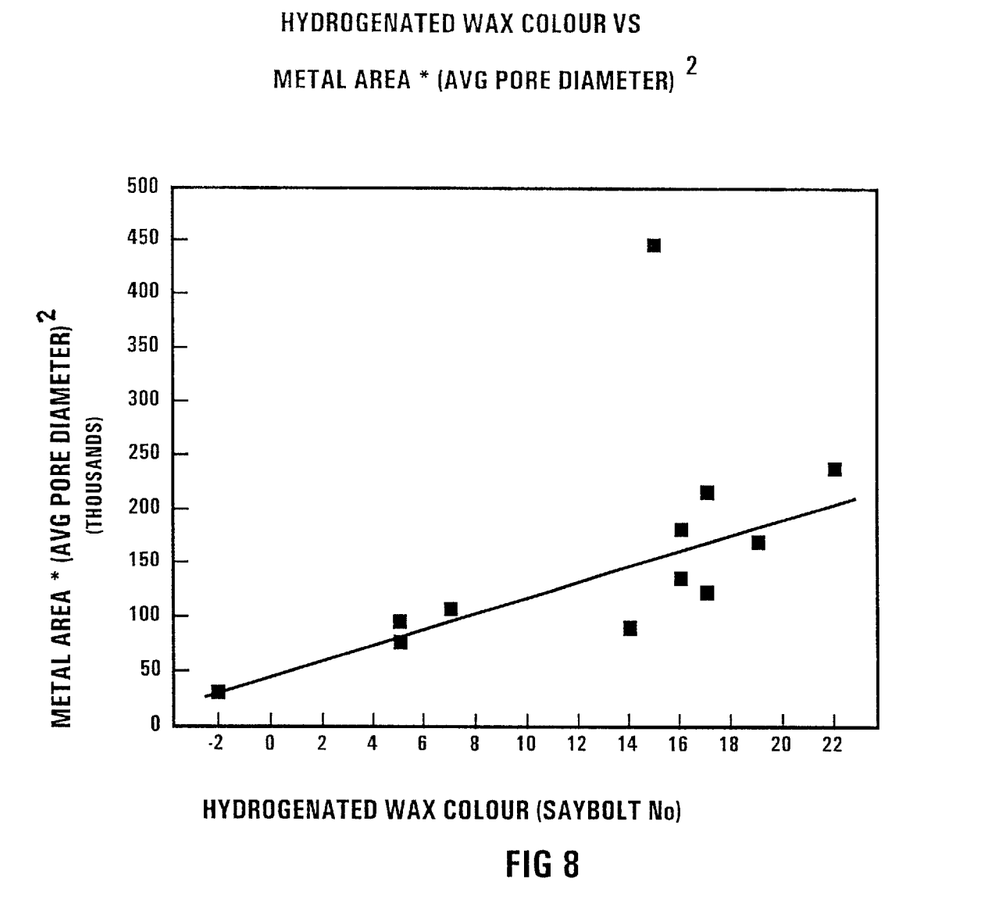
FIG. 8 shows, in respect of some of the hydrogenation catalysts of Examples 1 to 12, catalyst performance vs total metal area of the active compound and the average pore size of the catalyst.

This correlation is shown in FIG. 8. Here, it is evident that if both the metal area of the active component and the average pore size of the was hydrogenation catalyst are taken into account, a correlation with the was colour is possible.

This thus means that the pore size of the wax hydrogenation catalyst has a dual role. Smaller pore sizes result in higher dispersions, which contribute favourably to the dispersion of the active metal component of the catalyst, and therefore contribute favourably to the overall catalyst performance. Smaller pore sizes, on the other hand, have a negative effect on the catalyst performance due to their negative effect on the diffusion of the wax molecules into and out of the catalyst pores.

An effective long chain hydrocarbon hydrogenation catalyst must therefore preferably be prepared (impregnation of the active component and drying) at sub-atmospheric pressure, and have a careful manipulation of the pore size distribution, with particular emphasis on the amount of small (micropores) and large (macropores) pores. The small pores will ensure a high metal (active component) area while the large pores will facilitate the diffusion of the long chain hydrocarbon molecules.

EXAMPLE 13

A batch of 12 kg of the catalyst described in Example 2 was prepared following a similar recipe although on a larger scale. This catalyst was tested in a slurry bed pilot plant reactor 12 with a narrow reactor portion diameter of 5 cm and height of 12 m. 8 kg of catalyst were loaded into the reactor, and the wax to be hydrogenated was fed at a rate of 25 kg per hour. Hydrogen was co-fed at a rate of 35 $m^3{}_n$ per hour and the continuous reaction took place at 240° C. and a pressure of 30 bar. The catalyst was then separated from the wax by means of a known solid particle separation system.

The upward liquid velocity in the lower reaction portion 14 was calculated at 13 cm/s, while, in the upper reaction portion 16, it was calculated as being 0.4 cm/s. The liquid velocity along the transport section 38 of the downcomer 34 was calculated at about 2 m/s.

It is believed that for a successful commercial application of this invention, a Saybolt colour in excess of 15 after 60 days on line and less than 5 ppm of Ni in the filtered, hydrogenated wax, are required. The results obtained in this pilot plant slurry bed reactor test using the catalyst described in Example 2 were a Saybolt colour of between 18 to 20 after 60 days on line and less than 1 ppm of Ni in the filtered wax. This shows that the catalyst has the required overall catalytic performance and mechanical strength to be successfully used in a large scale.

As shown in Table 1, the same catalyst, ie the catalyst of Example 2, gave a Saybolt colour of 17 when tested in the laboratory or micro slurry bed hydrogenation reactor.

Therefore, and in view of the results obtained in the pilot plant slurry bed hydrogenation reactor, the wax hydrogenation catalyst should preferably give a hydrogenated Fishcer-Tropsch wax Saybolt number of 17 or higher, when tested in the micro slurry bed hydrogenation reactor.

A good hydrogenation catalyst must therefore preferably have, according to FIG. 8, an OCPF equal to or higher than 200 000.

To further ascertain the beneficial effect of macropores in the carrier, two carriers were prepared in which the proportion of macropores was increased in one of the carriers without disturbing the proportion of micropores and mesopores present. The preparation of these two catalyst is described below in Examples 14 and 15.

EXAMPLE 14

A spraydried alumina support was prepared by adding 100 g of Pural SB (trademark) obtainable from Condea Chemie GmbH to 800 ml distilled water. The pH was adjusted to 3.7 with acetic acid and the slurry allowed to stir for 2 hours. The pH was then increased to 6.0 with ammonium hydroxide and the viscosity adjusted with 800 ml distilled water. The $Al_2O_3$ gel was then spraydried. The support was calcined in air at 800° C. for 16 hours in an oven. A catalyst was prepared from this support in similar fashion to that of Example 1, except that the spraydried support was used instead of Puralox SCCa 5/150 (trademark).

EXAMPLE 15

The preparation of this support and of a catalyst therefrom, was similar to that of Example 14, except as regards to the following:

1. 10 g of carbon black (Corax N110) (trademark), obtainable from Algorax (Pty) Limited, J. Tallant Road, Deal Party, Port Elizabeth, South Africa were predispersed in 100 μml distilled water and then added to the slurry before lowering the pH to 3.7.
2. The support was calcined in air for 3 hours at 400° C. followed by 1 hour at 450° C., 1 hour at 500° C. and 8 hours at 800° C. This calcination procedure controlled the combustion rate of the carbon black, creating new pores without breaking up the particles due to too rapid evolution of gases.

The effect of the carbon black (Corax N110) addition as described in Example 15 is to increase the proportion of macropores without having an effect on the rest of the pore size distribution. The pores with a diameter above 209 Å only contribute about 4% of the total pore volume for the catalyst described in Example 14. These larger pores (above 209 Å), on the other hand, contribute about 16% of the total pore volume for the catalyst described in Example 15.

These catalysts were reduced, as previously described, at 380° C., and tested in the micro slurry bed reactor in the same manner in which the catalysts of Examples 1 to 12 were tested. The wax hydrogenated using the catalyst described in Example 15 gave a Saybolt number 4 units higher than the wax hydrogenated using the catalyst described in Example 14, therefore confirming the beneficial influence of the macropores in the overall performance of the catalyst.

Therefore, if the pore size distribution of the carrier has been manipulated with Pore Modifying Agents (PMA) to increase the amount of macropores, without disturbing the rest of the pore size distribution, the acceptable minimum OCPF could be lower.

The mechanical strength of the catalysts described in Examples 2 and 6 is shown in Table 2. Here, the mechanical strength is measured by means of the Jet Impingement Test. In this test, 100 g of the catalyst to be tested is loaded into a feeder. A stirrer located at the bottom of the feeder ensures that a constant flow of catalyst is sucked into a line in which air is fed upstream at a pressure of 2 bar. The air flow impinges a continuous and constant amount of catalyst against a steel plate. The breakage of the catalyst particles upon impingement is directly related to their mechanical strength. The percentage of broken particles is determined by measuring the particle size distribution before and after the jet impingement test by means of a Microtrac ASVR (trademark) manufactured by Leeds+Northrup.

TABLE 2

| ATTRITION TEST RESULTS (Jet Impingement) | | |
|---|---|---|
| PARTICLE SIZE | Change in % Fines | |
| (microns) | Example 2 | Example 6 |
| 66 | 12,28 | 28,54 |
| 44 | 7,69 | 23,15 |
| 22 | 4,00 | 12,45 |
| 11 | 3,00 | 7,78 |
| 5,5 | 2,12 | 5,03 |
| 1 | 0,55 | 1,69 |

The percentual change in the 22 microns particle fraction for the catalyst described in Example 2 is 4%, while the same change for the catalyst described in Example 6 is 12.45%. Based on known experience in slurry bed reactors, catalysts which show a percentual change in the 22 microns fraction of higher than 12%, show a breakage of the catalyst particles under the hydrodynamic conditions experienced in the slurry bed large scale reactors. The breakage percentage of the catalyst described in Example 6 is typical of catalysts in which the carrier is composed by peptised non-pourous alumina or silica nano-particles, either spray dried directly to the required particle size or calcined as a cake, followed by crushing to the desired particles size (eg the catalysts whose preparations are described in Examples 6 and 12).

The catalyst described in Example 2 is adequate from a mechanical strength point of view. Therefore, the mechanical strength of the family of catalysts which are part of this invention should preferably be similar or better than that of the catalyst of Example 2.

The hydrogenation of long chain hydrocarbons requires contact thereof with hydrogen in the presence of a solid catalyst. These reactions are more effective when smaller catalyst particle sizes are used although the separation of hydrocarbons from the catalyst is more difficult. It is known that for catalyst particle sizes below approximately 100 microns there is no further significant improvement in reaction rate per unit mass of catalyst.

For particle sizes less than about 2 millimeters it becomes impossible to contain the particles in a static bed of catalyst without encountering very high pressure drops and the catalyst size is usually selected to optimise the pressure drop across the catalyst bed. This results in a typical catalyst pellet size of 2 mm or larger for static beds, which results in a poor catalyst utilization due to diffusional limitations. A slurry bed reactor allows the use of much smaller particles, and therefore a more effective and economical catalyst utilization. In a slurry bed reactor, there is a continuous movement of these small catalyst particles with the passage of hydrocarbons and hydrogen through the catalyst bed. This inevitable movement of catalyst particles results in mechanical forces on the particles which tend to further break-up the catalysts to particle sizes below 10 micron which causes the separation of the catalyst from the liquid hydrocarbons to become more difficult.

This invention thus provides
(i) A method of producing a stronger catalyst with the required size and hydrogenation ability.
(ii) A concept of selecting a catalyst particle size which is a compromise between the optimums for catalyst reaction and solids separation performance
(iii) Use of a slurry bed reactor for the hydrogenation of long chain hydrocarbons as a continuous process.

What is claimed is:

1. A process for hydrogenating long chain hydrocarbon waxes, which process comprises
   continuously feeding a long chain hydrocarbon wax feedstock into a slurry bed comprising a slurry of catalyst particles in a slurrying liquid, with the slurry bed being contained in a reaction zone and the feedstock entering the reaction zone at a low level;
   continuously feeding a hydrogenation component into the slurry bed, also at a low level;
   allowing the hydrogenation component to react with the feedstock, thereby to hydrogenate the feedstock, as the feedstock and hydrogenation component pass upwardly through the slurry bed;
   withdrawing hydrogenated waxes from the reaction zone at a high level, as a hydrogenated product, with the catalyst particles having an Overall Catalyst Performance Factor ('OCPF') such that the Saybolt colour of the hydrogenated products is in excess of 15; and
   withdrawing any excess hydrogenation component from the reaction zone at a high level.

2. A process according to claim 1, wherein the wax feedstock is a wax fraction obtained as a product when a synthesis gas is subjected to Fisher-Tropsch reaction conditions, with the wax fraction comprising hydrocarbon molecules containing more than 20 carbon atoms, and having a congealing point exceeding 90° C., and with the OCPF of the catalyst particles being at least 200000.

3. A process according to claim 2, wherein the feedstock is in liquid form and is at a temperature between 100° C. and 350° C., and wherein it is fed into the reaction zone at such a rate as to provide a weight hourly space velocity of at least 0.5 in the reaction zone.

4. A process according to claim 2, wherein the hydrogenation component is in gaseous form, and is a hydrogen gas stream or a gas stream rich in hydrogen, with the gas stream being fed into the reaction zone at such a rate that its superficial velocity through the slurry bed is at least 1 cm/s.

5. A process according to claim 1, wherein the concentration of the catalyst particles in the slurry bed is between 10 mass % and 50 mass %, based on the total slurry bed mass, while the slurry bed is maintained at a temperature between 180° C. and 300° C., and the reaction zone is maintained at a pressure between 10 atmospheres and 50 atmospheres.

6. A processing according to claim 1, wherein the catalyst particles have a size distribution between 1 and 250 microns.

7. A process according to claim 6, wherein the catalyst particles have a size distribution between 30 and 170 microns.

8. A processing according to claim 1, wherein the catalyst is that obtained by
   (i) subjecting a slurry, comprising a particulate alumina or silica carrier, a nickel compound as an active component and a solvent for the active component, to a sub-atmospheric pressure environment, thereby to impregnate the carrier with the active component;
   (ii) drying the impregnated carrier in a sub-atmospheric pressure environment; and
   (iii) calcining the dried impregnated carrier, thereby to obtain a hydrogenation catalyst suitable for use in the hydrogenation process.

9. A processing according to claim 1, wherein the catalyst particles have sufficient strength such that a fraction of the particles having particle sizes of 22 microns and below has a percentual change in particle size of not higher than 12% when subjected to a jet impingement test in which the catalyst particles are impinged against a metal plate by means of an air stream having a pressure of 2 bar.

10. A process for hydrogenating long chain hydrocarbon waxes, which process comprises:
    continuously feeding a long chain hydrocarbon wax feedstock into a slurry bed contained in a reaction zone, the slurry bed comprising a slurry of catalyst particles in a slurrying liquid, and the feedstock enerting the reaction zone at a low level, the catalyst particles having sufficient strength such that a fraction of the particles having particle sizes of 22 microns and below has a percentual change in particle size of not higher than 12% when subjected to a jet impingement test in which the catalyst particles are impinged against a metal plate by means of an air stream having a pressure of 2 bar;
    continuously feeding a hydrogenation component into the slurry bed, also at a low level;
    allowing the hydrogenation component to react with the feedstock, thereby to hydrogenate the feedstock, as the feedstock and hydrogenation component pass upwardly through the slurry bed;
    withdrawing hydrogenated waxes from the reaction zone at a high level, as a hydrogenated product, with the catalyst particles having an Overall Catalyst Performance Factor ('OCPF') such that the Saybolt color of the hydrogenated product is in excess of 15; and
    withdrawing any excess hydrogenation component from the reaction zone at a high level.

11. A process according to claim 10, wherein the wax feedstock is a wax fraction obtained as a product when a synthesis gas is subjected to Fischer-Tropsch reaction conditions, with the wax fraction comprising hydrocarbon molecules containing more than 20 carbon atoms, and having a congealing point exceeding 90° C., and with the OCPF of the catalyst particles being at least 200000.

12. A process according to claim 11, wherein the feedstock is in liquid form and is at a temperature between 100° C. and 350° C., and wherein it is fed into the reaction zone at such a rate as to provide a weight hourly space velocity of at least 0.5 in the reaction zone.

13. A process according to claim 11, wherein the hydrogenation component is in gaseous form, and is a hydrogen gas stream or a gas stream rich in hydrogen, with the gas stream being fed into the reaction zone at such a rate that its superficial velocity through the slurry bed is at least 1 cm/s.

14. A process according to claim 10, wherein the concentration of the catalyst particles in the slurry bed is between 10 mass % and 50 mass %, based on the total slurry bed mass, while the slurry bed is maintained at a temperature between 180° C. and 300° C., and the reaction zone is maintained at a pressure between 10 atmospheres and 50 atmospheres.

15. A process according to claim 10, wherein the catalyst particles have a size distribution between 1 and 250 microns.

16. A process according to claim 15, wherein the catalyst particles have a size distribution between 30 and 170 microns.

17. A process according to claim 10, wherein the catalyst is that obtained by
   (i) subjecting a slurry, comprising a particulate alumina or silica carrier, a nickel compound as an active component and a solvent for the active component, to a sub-atmospheric pressure environment, thereby to impregnate the carrier with the active component;
   (ii) drying the impregnated carrier in a sub-atmospheric pressure environment; and
   (iii) calcining the dried impregnated carrier, thereby to obtain a hydrogenation catalyst suitable for use in the hydrogenation process.

18. A hydrogenated product, when produced by the process of claim 1.

* * * * *